(12) United States Patent
Linnen et al.

(10) Patent No.: US 6,638,714 B1
(45) Date of Patent: Oct. 28, 2003

(54) OLIGONUCLEOTIDE PRIMERS FOR EFFICIENT DETECTION OF HEPATITIS C VIRUS (HCV) AND METHODS OF USE THEREOF

(75) Inventors: Jeffrey M. Linnen, San Diego, CA (US); Kevin M. Gorman, Penfield, NY (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 0 days.

(21) Appl. No.: 09/493,353

(22) Filed: Jan. 28, 2000

Related U.S. Application Data

(60) Provisional application No. 60/118,497, filed on Feb. 3, 1999.

(51) Int. Cl.[7] .......................... C12Q 1/68; C07H 21/04
(52) U.S. Cl. ........................... 435/5; 435/6; 435/91.2; 536/23.1; 536/24.3
(58) Field of Search .............. 435/91.2, 6, 5; 536/23.1, 24.3

(56) References Cited

U.S. PATENT DOCUMENTS

| | | | | |
|---|---|---|---|---|
| 5,837,442 A | * | 11/1998 | Tsang | 435/5 |
| 5,837,463 A | * | 11/1998 | Tanaka et al. | 435/6 |
| 5,846,704 A | * | 12/1998 | Maertens et al. | 435/5 |

FOREIGN PATENT DOCUMENTS

| | | | | |
|---|---|---|---|---|
| EP | 0776981 | 6/1997 | ............ | C12Q/1/68 |
| WO | WO 93/13224 | 6/1993 | ............ | C12Q/1/68 |
| WO | WO 97/46716 | 12/1997 | ............ | C12Q/1/70 |

OTHER PUBLICATIONS

Han et al "Characterization of the terminal regions of HCV RNA" PNAS, vol. 88, p. 1711–1715, Mar. 1991.*

Kolykhalov et al "Identification of a highly conserved sequence element at the 3' terminus of HCV genome RNA" J. of Virology, vol. 70, No. 6, p. 3363–3371, Jun. 1996.*

Encke et al "Total chemical syntheis of the 3' UTR of the HCV with long oligodeoxynucleotides" J. of Virological Methods, vol. 74, No. 1, p. 117–121, Sep. 1998.*

Ahern, www.thescientist.library.upenn.edu/yr1995/july/tools_950724.htlm, Dec. 22, 1998.*

Young, et al., 1993, *J. Clin. Microbiol.* 31(4):882.

Myers et al., 1991, *Biochemistry.* 30(3):7661.

Yoo et al., 1989, *J. Biol. Chem.* 764:17078.

Matteucci et al., 1981, *J. Am. Chem. Soc.* 103:3185.

Bukh J. et al.; "Importance of primer selection for the detection of Hepatitis C virus RNA with the polymerase chain reaction assay"; *Proceedings of the National Academy of Sciences of USA*, US, National Academy of Science. Washington, vol. 89, 1992, pp. 187–191.

Karachristos A. et al.; Detection and analysis of Hepatitis C virus by a combined RT–PCR method: variation in the 5' non–coding region of the viral genome; *Journal of Medicinal Microbiology*, vol. 42, 1995, pp. 367–371.

Roth W. K. et al.; "Comparison of two quantitative Hepatitis C virus reverse transcriptase assays", *J. of Clinical Microbiology*, vol. 34, No. 2, 1996, pp. 261–264.

Ruster B. et al.; "Quantification of Hepatitis C virus RNA by competitive reverse transcription and polymerase chain reaction using a modified Hepatitis C virus RNA transcript"; *Analytical Biochemistry*, US, Academic Press, San Diego, DA, vol. 224, No. 2, Jan. 20, 1995, pp. 597–600.

Walker F. M. et al.; "Detection and localization of in situ molecular biology techniques and immunohistochemistry of Hepatitis C virus in livers of chronically infected patients"; *The Journal of Histochemistry & Cytochemistry*, vol. 46, No. 5, 1998, pp. 653–660.

Yoshioka K. et al.; "Detection of Hepatitis C virus by polymerase chain reaction and response to interferon –X therapy: relationship to genotypes of Hepatitis C virus"; *Hepatology*, US, Williams and Wilkins, Baltimore, MD; vol. 16, No. 2, Aug. 1, 1992, pp. 293–299.

* cited by examiner

*Primary Examiner*—Gary Benzion
*Assistant Examiner*—Jeanine Goldberg
(74) *Attorney, Agent, or Firm*—Darby & Darby

(57) ABSTRACT

Described herein are methods and kits for the detection of hepatitis C virus RNA is biological samples obtained from human subjects. The invention includes novel amplification primers and probes useful in the amplification of DNA derived from hepatitis C virus RNA, and kits and methods which incorporate the novel primers.

42 Claims, No Drawings

US 6,638,714 B1

OLIGONUCLEOTIDE PRIMERS FOR EFFICIENT DETECTION OF HEPATITIS C VIRUS (HCV) AND METHODS OF USE THEREOF

This application claims priority under 35 U.S.C. § 119(e) to U.S. Provisional Patent Application Ser. No. 60/118,497 filed Feb. 3, 1999.

FIELD OF THE INVENTION

The present invention pertains to improved methods for detecting nucleic acid sequences in biological samples, particularly sequences derived from infectious microorganisms.

BACKGROUND OF THE INVENTION

Hepatitis C Virus (HCV) is a parenterally transmitted virus responsible for the majority of cases of post-transfusion hepatitis and a substantial portion of sporadic (or community acquired) hepatitis cases worldwide. It is estimated that more than 1% of the world's population is infected with HCV. HCV infection is associated with acute hepatitis, chronic hepatitis, cirrhosis, and hepatocellular carcinoma.

HCV is currently classified as a separate genus, Hepacivirus, in the family Flaviviridae. Its genome consists of a positive-stranded RNA molecule of about 9,500 nucleotides with a single, large open reading frame (ORF) which encodes a polyprotein precursor of about 3,000 amino acids. The large ORF is preceded by a 5' non-coding region (NCR) of about 340 nucleotides, which is the most highly conserved region of the genome. The 5' region of the ORF encodes (in a 5'-to-3' direction) a capsid protein, two envelope glycoproteins (E1 and E2), and a small protein of unknown function (P7). The 3' portion of the ORF encodes nonstructural proteins which include a protease, protease/helicase bi-functional protein, RNA polymerase, and regulatory peptides. The 3' portion also includes an NCR.

Analysis of HCV coding sequences from around the world has revealed considerable sequence variation among individual viral isolates. Furthermore, analyses of HCV sequences from individual patients have shown that the virus circulates as so-called "quasi-species," which contain related but not identical sequences. The variation that exists among isolates and within individual patients is believed to be the result of the low fidelity of the virally-encoded RNA-dependent RNA polymerase. The degree of genetic variability of HCV has important implications for prevention, diagnosis, and control of infection.

Serodiagnosis of HCV infection is typically determined by commercially available enzyme immuno-assays (EIA) which detect antibodies that bind recombinant HCV proteins or peptides. Positive EIA results can be confirmed by a recombinant immunoblot assay (RIBA), but neither EIA nor RIBA assays distinguish past from present infections. Because of the typically low titer of circulating virus, a direct assay for viral proteins has not been successfully developed. Furthermore, antibody-based assays fail to detect HCV infection for usually 2 to 3 months after exposure Thus, there is a need in the art for improved assays for HCV that are sensitive enough to detect HCV viremia within a few days after initial exposure of a patient to HCV.

SUMMARY OF THE INVENTION

Thus, in a first aspect, the invention is directed to a method for detecting the presence of Hepatitis C Virus (HCV) RNA in a biological sample. The method comprises:

(A) performing a reverse transcription reaction using as a template RNA derived from the sample to produce HCV-specific reverse transcription products;

(B) amplifying the reverse-transcription products using one or more pairs of oligonucleotide primers specific for HCV to produce HCV-specific amplification products, where each of the pairs comprises:

(a) a forward primer selected from the group consisting of:

(i) 5'-CAGAAAGCGTCTAGCCATGGCGTTAGTA-3'
(C69F28) <SEQ ID NO. 1>, (ii) 5'-GGGAGAGCCATAGTGGTCTGCGGAA-3'
(C131F25) <SEQ ID NO. 2>, and (iii) 5'-GTGGTCTGCGGAACCGGTGAGTACAC-3
(C143F26) <SEQ ID NO. 3>; and (b) a reverse primer selected from the group consisting of:

(i) 5'-CGGTTCCGCAGACCACTATGGCTCTC-3'
(C133R26) <SEQ ID NO. 4>, (ii) 5'-GCAAGCACCCTATCAGGCAGTACCACA-3'
(C282R27) <SEQ ID NO. 5>, (iii) 5'-CACTCGCAAGCACCCTATCAGGCAGTA-3'
(C287R27) <SEQ ID NO. 6>, and (iv) 5'-CGGGGCACTCGCAAGCACCCTATCA-3'
(C294R25) <SEQ ID NO. 7>; and (C) detecting the amplification products, where detection of the amplification products indicates the presence of HCV RNA in the sample.

In another aspect, the invention is directed to a method for amplifying Hepatitis C Virus (HCV) DNA. The method comprises:

(A) performing a polymerase chain reaction on a DNA sample containing HCV DNA using one or more pairs of oligonucleotide primers specific for HCV to produce HCV-specific amplification products, where each of the pairs comprises:

(a) a forward primer selected from the group consisting of:

(i) 5'-CAGAAAGCGTCTAGCCATGGCGTTAGTA-3'
(C69F28) <SEQ ID NO. 1>, (ii) 5'GGGAGAGCCATAGTGGTCTGCGGAA-3'
(C131F25) <SEQ ID NO. 2>, and (iii) 5'-GTGGTCTGCGGAACCGGTGAGTACAC-3
(C143F26) <SEQ ID NO. 3>; and (b) a reverse primer selected from the group consisting of:

(i) 5'-CGGTTCCGCAGACCACTATGGCTCTC-3'
(C133R26) <SEQ ID NO. 4>, (ii) 5'-GCAAGCACCCTATCAGGCAGTACCACA-3'
(C282R27) <SEQ ID NO. 5>, (iii) 5'-CACTCGCAAGCACCCTATCAGGCAGTA-3'
(C287R27) <SEQ ID NO. 6>, and -continued (iv) 5'-CGGGGCACTCGCAAGCACCCTATCA-3'
(C294R25) <SEQ ID NO. 7>.

In a third aspect, the invention is directed to a method for detecting the presence of Hepatitis C Virus (HCV) RNA in a biological sample. The method comprises:

(A) performing a reverse transcription reaction using as a template RNA derived from the sample to produce HCV-specific reverse transcription products;

(B) amplifying the reverse-transcription products using a forward primer and a reverse primer to produce HCV-specific amplification products, where the forward primer consists of the oligonucleotide 5'-GGTGGCTCCATCTTAGCCCTAGTCACG-3' (1F27) <SEQ ID NO. 8> and the reverse primer consists of the oligonucleotide 5'-AGGCCAGTATCAGCACTCTCTGCAGTC-3' (57R27) <SEQ ID NO. 9>; and (C) detecting the amplification products, where detection of the amplification products indicates the presence of HCV RNA in the sample.

In a fourth aspect, the invention is directed to a method for amplifying Hepatitis C Virus (HCV) DNA. The method comprises:

(A) performing a polymerase chain reaction on a DNA sample containing HCV DNA using a forward primer and a reverse primer to produce HCV-specific amplification products, where the forward primer consists of the oligonucleotide 5'-GGTGGCTCCATCTTAGCCCTAGTCACG-3' (1F27) <SEQ ID NO. 8> and the reverse primer consists of the oligonucleotide 5'-AGGCCAGTATCAGCACTCTCTGCAGTC-3' (57R27) <SEQ ID NO. 9>.

In a fifth aspect, the invention is directed to a method for detecting the presence of Hepatitis C Virus (HCV) RNA in a biological sample. The method comprises:

(A) performing a reverse transcription reaction using as a template RNA derived from the sample to produce HCV-specific reverse transcription products;

(B) amplifying the reverse-transcription products using one or more pairs of 5' NCR oligonucleotide primers specific for HCV and one or more pairs of 3' NCR oligonucleotide primers to produce HCV-specific amplification products, where each of the pairs of 5' NCR oligonucleotide primers comprises:
(a) a forward primer selected from the group consisting of:

(i) 5'-CAGAAAGCGTCTAGCCATGGCGTTAGTA-3'
(C69F28) <SEQ ID NO. 1>, (ii) 5'-GGGAGAGCCATAGTGGTCTGCGGAA-3'
(C131F25) <SEQ ID NO. 2>, and (iii) 5'-GTGGTCTGCGGAACCGGTGAGTACAC-3
(C143F26) <SEQ ID NO. 3>; and (b) a reverse primer selected from the group consisting of:

(i) 5'-CGGTTCCGCAGACCACTATGGCTCTC-3'
(C133R26) <SEQ ID NO. 4>, (ii) 5'-GCAAGCACCCTATCAGGCAGTACCACA-3'
(C282R27) <SEQ ID NO. 5>, (iii) 5'-CACTCGCAAGCACCCTATCAGGCAGTA-3'
(C287R27) <SEQ ID NO. 6>, and (iv) 5'-CGGGGCACTCGCAAGCACCCTATCA-3'
(C294R25) <SEQ ID NO. 7>; and where each of the pairs of 3' NCR oligonucleotide primers comprises a forward primer consisting of the oligonucleotide 5'-GGTGGCTCCATCTTAGCCCTAGTCACG-3' (1F27) <SEQ ID NO. 8> and a reverse primer consisting of the oligonucleotide 5'-AGGCCAGTATCAGCACTCTCTGCAGTC-3 (57R27) <SEQ ID NO. 9>; and (c) detecting the amplification products, where detection of the amplification products indicates the presence of HCV RNA in the sample.

In a sixth aspect, the invention is directed to a method for amplifying Hepatitis C Virus (HCV) DNA. The method comprises:

(A) performing a polymerase chain reaction on a DNA sample containing HCV DNA using one or more pairs of 5' NCR oligonucleotide primers specific for HCV and one or more pairs of 3' NCR oligonucleotide primers to produce HCV-specific amplification products, where each of the pairs of 5' NCR oligonucleotide primers comprises:
(a) a forward primer selected from the group consisting of:

(i) 5'-CAGAAAGCGTCTAGCCATGGCGTTAGTA-3'
(C69F28) <SEQ ID NO. 1>, (ii) 5'-GGGAGAGCCATAGTGGTCTGCGGAA-3'
(C131F25) <SEQ ID NO. 2>, or (iii) 5'-GTGGTCTGCGGAACCGGTGAGTACAC-3
(C143F26) <SEQ ID NO. 3>; and (b) a reverse primer selected from the group consisting of:

(i) 5'-CGGTTCCGCAGACCACTATGGCTCTC-3'
(C133R26) <SEQ ID NO. 4>, (ii) 5'-GCAAGCACCCTATCAGGCAGTACCACA-3'
(C282R27) <SEQ ID NO. 5>, (iii) 5'-CACTCGCAAGCACCCTATCAGGCAGTA-3'
(C287R27) <SEQ ID NO. 6>, or (iv) 5'-CGGGGCACTCGCAAGCACCCTATCA-3'
(C294R25) <SEQ ID NO. 7>; and where each of the pairs of 3' NCR oligonucleotide primers comprises a forward primer consisting of the oligonucleotide 5'-GGTGGCTCCATCTTAGCCCTAGTCACG-3' (1F27) <SEQ ID NO. 8> and a reverse primer consisting of the oligonucleotide 5'-AGGCCAGTATCAGCACTCTCTGCAGTC-3 (57R27) <SEQ ID NO. 9>.

In some embodiments of the method, where a reverse transcription reaction is performed, the reverse transcription reaction is performed using random oligonucleotide primers, alternatively, one or more HCV-specific reverse transcription primers, i.e., oligonucleotides having sequences that correspond to sequences in HCV RNA, may be used. Methods for detection of amplification include, without limitation, (a) electrophoresis and (b) capture of amplification products on a solid support to which HCV-specific probes are attached followed by quantifying the bound products using a colorimetric assay.

In a further aspect, the invention is directed to a kit for amplifying HCV DNA derived from HCV RNA. The kit comprises one or more pairs of 5' NCR oligonucleotide primers, where each of the pairs of 5' NCR oligonucleotide primers comprises:

(a) a forward primer selected from the group consisting of:

(i) 5'-CAGAAAGCGTCTAGCCATGGCGTTAGTA-3'
(C69F28) <SEQ ID NO. 1>, (ii) 5'-GGGAGAGCCATAGTGGTCTGCGGAA-3'
(C131F25) <SEQ ID NO. 2>, and (iii) 5'-GTGGTCTGCGGAACCGGTGAGTACAC-3
(C143F26) <SEQ ID NO. 3>; and (b) a reverse primer selected from the group consisting of:

(i) 5'-CGGTTCCGCAGACCACTATGGCTCTC-3'
(C133R26) <SEQ ID NO. 4>, (ii) 5'-GCAAGCACCCTATCAGGCAGTACCACA-3'
(C282R27) <SEQ ID NO. 5>, (iii) 5'-CACTCGCAAGCACCCTATCAGGCAGTA-3'
(C287R27) <SEQ ID NO. 6>, and (iv) 5'-CGGGGCACTCGCAAGCACCCTATCA-3'
(C294R25) <SEQ ID NO. 7>.

In a further aspect, the invention is directed to a kit for amplifying HCV cDNA derived from HCV RNA. The kit comprises one or more pairs of 3' NCR oligonucleotide primers, where each of the pairs of 3' NCR oligonucleotide primers comprises a forward primer consisting of the oligonucleotide 5'-GGTGGCTCCATCTTAGCCCTAGTCACG-3' (1F27) <SEQ ID NO. 8> and a reverse primer consisting of the oligonucleotide 5'-AGGCCAGTATCAGCACTCTCTGCAGTC-3 (57R27) <SEQ ID NO. 9>.

In an alternate aspect, the invention is directed to a kit for detecting the presence of HCV DNA. The kit comprises one or more pairs of 5' NCR oligonucleotide primers, where each of the pairs of 5' NCR oligonucleotide primers comprises:

a forward primer selected from the group consisting of:

(i) 5'-CAGAAAGCGTCTAGCCATGGCGTTAGTA-3'
(C69F28) <SEQ ID NO. 1>, (ii) 5'-GGGAGAGCCATAGTGGTCTGCGGAA-3'
(C131F25) <SEQ ID NO. 2>, or (iii) 5'-GTGGTCTGCGGAACCGGTGAGTACAC-3
(C143F26) <SEQ ID NO. 3>; and (b) a reverse primer selected from the group consisting of:

(i) 5'-CGGTTCCGCAGACCACTATGGCTCTC-3'
(C133R26) <SEQ ID NO. 4>, (ii) 5'-GCAAGCACCCTATCAGGCAGTACCACA-3'
(C282R27) <SEQ ID NO. 5>, (iii) 5'-CACTCGCAAGCACCCTATCAGGCAGTA-3'
(C287R27) <SEQ ID NO. 6>, and (iv) 5'-CGGGGCACTCGCAAGCACCCTATCA-3'
(C294R25) <SEQ ID NO. 7>.

In yet another aspect, the invention is directed to a kit for detecting the presence of HCV RNA. The kit comprises one or more pairs of 3' NCR oligonucleotide primers, where each of the pairs of 3' NCR oligonucleotide primers comprises a forward primer consisting of the oligonucleotide 5'-GGTGGCTCCATCTTAGCCCTAGTCACG-3' (1F27) <SEQ ID NO. 8> and a reverse primer consisting of the oligonucleotide 5'-AGGCCAGTATCAGCACTCTCTGCAGTC-3 (57R27) <SEQ ID NO. 9>.

DETAILED DESCRIPTION OF THE INVENTION

The present inventors have discovered that detection of Hepatitis C Virus (HCV) RNA in biological samples is more efficient when oligonucleotides having sequences complementary to certain sequences present in HCV RNA are used as primers for amplification. The present invention thus provides an improved single-round, reverse transcription/amplification assay which detects low copy levels of HCV RNA. Oligonucleotide primers are selected based on theoretical considerations of sequence conservation, intra- and inter-molecular interactions, and the predicted secondary structures of the amplicon and surrounding sequence. Furthermore, the primers and assay system are designed to allow the co-amplification (and co-detection) of multiple regions of the HCV genome, multiple viral species, and an internal positive control (IPC) RNA (or DNA). Simultaneous amplification/detection of multiple regions of the HCV genome increases assay sensitivity and the co-amplification of an IPC decreases the likelihood of false negative results because of PCR inhibition.

Many techniques in molecular biology, microbiology, recombinant DNA, and protein biochemistry are used in practicing the present invention, such as those explained in, for example, *Current Protocols in Molecular Biology,* Volumes I, II, and III, 1997 (F. M. Ausubel ed.); Sambrook et al., 1989, *Molecular Cloning: A Laboratory Manual,* Second Edition, Cold Spring Harbor Laboratory Press, Cold Spring Harbor, N.Y.; *DNA Cloning: A Practical Approach,* Volumes I and II, 1985 (D. N. Glover ed.); *Oligonucleotide Synthesis,* 1984, (M. L. Gait ed.); *Transcription and Translation,* 1984 (Hames and Higgins eds.); *A Practical Guide to Molecular Cloning,* the series, *Methods in Enzymology* (Academic Press, Inc.); and *Protein Purification: Principles and Practice,* Second Edition (Springer-Verlag, N.Y.).

"Nucleic acid" or "polynucleotide" as used herein refers to purine- and pyrimidine-containing polymers of any length, either polyribonucleotides or polydeoxyribonucleotides or mixed polyribo-polydeoxyribo nucleotides. This includes single- and double-stranded molecules, such as, for example, DNA-DNA, DNA-RNA and RNA-RNA hybrids, as well as "protein nucleic acids" (PNA) formed by conjugating bases to an amino acid backbone. This also includes nucleic acids containing modified bases.

A "complement" of a nucleic acid sequence as used herein refers to the antisense sequence that participates in Watson-Crick base-pairing with the original sequence.

A "primer" as used herein is an isolated oligonucleotide between about 10 and about 50 nucleotides in length, preferably between about 12 and about 25 nucleotides in length and most preferably between about 12 and about 18 nucleotides in length, that forms a duplex with a single-stranded nucleic acid sequence of interest and allows polymerization of a complementary strand using, e.g., reverse transcriptase or DNA polymerase.

An "isolated" nucleic acid as used herein refers to a component that is removed from its original environment (for example, its natural environment if it is naturally occurring or a reaction mixture if it is synthetic). An isolated nucleic acid typically contains less than about 50%, preferably less than about 75%, and most preferably less than about 90%, of the components with which it was originally associated.

A nucleic acid sequence that is "derived from" a designated sequence refers to a sequence that corresponds to a region of the designated sequence. This encompasses sequences that are homologous or complementary to the sequence.

An internal positive control (IPC) target nucleic acid refers to a synthetic nucleic acid sequence cloned into a plasmid vector which is subsequently linearized, typically by the action of a restriction endonuclease. An IPC will typically have multiple primer binding sequences surrounding a generic probe-binding region, and acts as a generic control against false negative results in nucleic acid amplification reactions.

The sequence of a preferred internal positive control target DNA is:

<SEQ ID NO. 10>

5'-

CGCCAGCGTGGACCATCAAGTAGTAATGAACGCACGGACGAGGACATCA

TAGAGATTACACCTTTATCCACAGTTCTCGGTCTAACGCAGCAGTCAGTG

TATCAGCACCAGCATCCGTAGTGAGTCTTCAGTGTCTGCTCCAGGATCGT

G-3'.

Nucleic acids comprising any of the sequences disclosed herein or subsequences thereof can be prepared by conventional methods. For example, DNA can be chemically synthesized using, e.g., the phosphoramidite solid support method of Matteucci et al., 1981, *J. Am. Chem. Soc.* 103:3185, the method of Yoo et al., 1989, *J. Biol. Chem.* 764:17078, or other well known methods. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) or charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. PNAs are also encompassed by the term "nucleic acid". The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

Amplification as used herein refers to an iterative process by which a nucleic acid is copied. Suitable methods for amplification include without limitation polymerase chain reaction, ligase chain reaction, strand displacement amplification, transcription mediated amplification, and nucleic acid single base amplification.

The present invention provides methods for detection of HCV in biological samples. The methods are carried out by
(i) performing a reverse transcription reaction using as a template RNA contained within or derived from the sample;
(ii) amplifying the reverse-transcription products using pairs of amplification primers having sequences corresponding to sequences within the 5' or 3' non-coding region of HCV RNA, to produce HCV-specific amplification products; and
(iii) detecting HCV-specific amplification products.

Detection of HCV-specific amplification products indicates the presence of HCV RNA in the sample.

According to the invention, a biological sample is obtained from a patient by any conventional means. Suitable biological samples include, without limitation, blood, serum, plasma, urine, breast milk, and cerebrospinal fluid. Preferably, plasma is used as the source of HCV RNA.

The biological sample is treated in any manner that provides access of the reverse transcription reagents to RNA, specifically HCV RNA, contained within the sample. RNA "derived from" a biological sample is any RNA which was originally present in the sample and to which access has been gained by treating the sample. Preferably, RNA is extracted from the sample using any method well known in the art, such as, e.g., methods employing guanidinium thiocyanate, or using commercially available reagents and methods such as, e.g., PureScript® from Gentra Systems, Inc. (Minneapolis Minn.). Any extraction procedure may be used that results in separation of the RNA from RNases, other proteins, and/or any other components that might interfere with reverse transcription.

The sample is then subjected to reverse transcription using (a) random primers, such as random hexamer primers obtainable from Pharmacia Biotech, Piscataway, N.J. and/or (b) primers derived from the 5' or 3' NCRs of the HCV RNA genomic sequence. Reverse transcription is carried out using conventional procedures, such as are described in *Current Protocols in Molecular Biology,* Volumes I, II, and III, 1997 (F. M. Ausubel ed.); in U.S. Pat. No. 5,322,770; in Young, et al., *J. Clin. Microbiol.* 31(4):882 (1993); Myers et al., *Biochemistry* 30(3):7661 (1991). Other primers suitable for use as reverse transcription primers, and methods for reverse transcription which can be used in the present invention include those described in copending U.S. patent application Serial No. 60/118,520.

Following the reverse transcription reaction, the products are amplified. Any method for amplification may be used, including, without limitation, polymerase chain reaction (PCR), ligase chain reaction, strand displacement reaction, nucleic acid single base amplification, and transcription mediated amplification. Preferably, PCR is used. Typically, a reaction mixture containing all of the necessary components for PCR is added directly to the reverse transcription reaction mixture. Amplification is then carried out using conditions specified by the primer pairs that are used.

The present inventors have discovered certain pairs of HCV-specific amplification primers are particularly advantageous in detecting HCV RNA in patient samples. Non-limiting examples of useful primers derived from the 5' NCR of the HCV genome include those listed in Table 1 below.

TABLE 1

| PRIMER  | SEQUENCE                          | LOC.        | S*  | SIN** |
|---------|-----------------------------------|-------------|-----|-------|
| C69f28  | 5'-CAGAAAGCGTCTAGCCATGGCGTTAGTA-3' | 69–96       | S   | 1     |
| C131F25 | 5'-GGGAGAGCCATAGTGGTCTGCGGAA-3'   | 131–155     | S   | 2     |
| C143R26 | 5'-GTGGTCTGCGGAACCGGTGAGTACAC-3'  | 143–168     | S   | 3     |
| C133F26 | 5'-CGGTTCCGCAGACCACTATGGCTCTC-3'  | 133–158     | AS  | 4     |
| C282R26 | 5'-GCAAGCACCCTATCAGGCAGTACCACA-3' | 282–308     | AS  | 5     |
| C287R27 | 5'-CACTCGCAAGCACCCTATCAGGCAGTA-3' | 287–313     | AS  | 6     |
| C294R25 | 5'-CGGGGCACTCGCAAGCACCCTATCA-3'   | 294–318     | AS  | 7     |

*Strand orientation: S = sense; AS = antisense; **Sequence ID No.

Any combination of sense and antisense oligonucleotides may be used as forward and reverse amplification primers, respectively. Preferred pairs of 5' NCR primers for use in amplification include:

(a)  5'-CAGAAAGCGTCTAGCCATGGCGTTAGTA-3'    <SEQ ID NO. 1> and

5'-CGGTTCCGCAGACCACTATGGCTCTC-3'     <SEQ ID NO. 4> and (b)  5'-GGGAGAGCCATAGTGGTCTGCGGAA-3'      <SEQ ID NO. 2> and

5'-CGGGGCACTCGCAAGCACCCTATCA-3'      <SEQ ID NO. 7>.

In one preferred embodiment, the pair of amplification primers consists of 5'-CAGAAAGCGTCTAGCCATGGCGTTAGTA-3' <SEQ ID NO. 1> and 5'-CGGTTCCGCAGACCACTATGGCTCTC-3' <SEQ ID NO. 4>. In another preferred embodiment, the pair of amplification primers consists of 5'-GGGAGAGCCATAGTGGTCTGCGGAA-3' <SEQ ID NO. 2> and 5'-CGGGGCACTCGCAAGCACCCTATCA-3' <SEQ ID NO. 7>.

Non-limiting examples of useful primers derived from the 3' NCR of the HCV genome include a forward primer consisting of 5'-GGTGGCTCCATCTTAGCCCTAGTCACG-3' (1F27) <SEQ ID NO. 8> and a reverse primer consisting of 5'-AGGCCAGTATCAGCACTCTCTGCAGTC-3' (57R27) <SEQ ID NO. 9>.

The invention also encompasses multiplex amplification, i.e., simultaneous amplification of different sequences using different sets of primers in the same reaction mixture. A preferred set of primer pairs that can be used simultaneously in a multiplex amplification reaction is:

(a)  5'-GGGAGAGCCATAGTGGTCTGCGGAA-3'      <SEQ ID NO.2> and

5'-CGGGGCACTCGCAAGCACCCTATCA-3'     <SEQ ID NO. 7> and
     (5' pair)

(b)  5'-GGTGGCTCCATCTTAGCCCTAGTCACG-3'   <SEQ ID NO. 8> and

5'-AGGCCAGTATCAGCACTCTCTGCAGTC-3'   <SEQ ID NO. 9>.
     (3' pair)

Following amplification, the amplified products may be detected using any method known in the art, including, without limitation, gel electrophoresis in agarose or acrylamide; non-isotopic colorimetric detection such as the SureCell□ system (see, e.g., Example 1 below); ECi detection; fluorescence, and chemiluminescence. Reagents useful in such detection methods are available from, e.g., Molecular Probes, Eugene, Oreg. and Ortho Clinical Diagnostics, Rochester, N.Y.

The detection of HCV-specific amplification products indicates the presence of HCV RNA in the sample. When gel electrophoresis is used, HCV-specific amplification products are confirmed by their size, as predicted by the location in HCV RNA of the sequences corresponding to the amplification primers used in the reaction. Useful HCV-specific 5' NCR capture probes useful for colorimetric detection include, without limitation, 5'-GGGTCCTGGAGGCTGCACGACACTCAT-3' <SEQ ID NO. 11>, 5'-CCTTTCGCGACCCAACACTACTCGGCT-3' <SEQ ID NO. 12>, and 5'-TTTCGCGACCCAACACTACTCGGCT-3' <SEQ ID NO. 13>. Useful HCV-specific 3' NCR capture probes include, without limitation, 5'-GCGGCTCACGGACCTTTCACAGCTA-3' <SEQ ID NO. 14> and 5'-ATGCGGCTCACGGACCTTTCACAGC-3' <SEQ ID NO. 15>.

Kits for amplifying HCV DNA derived from HCV RNA can be prepared containing one or more pairs of forward and reverse 5' NCR oligonucleotide primers, where the forward primers may be 5'-CAGAAAGCGTCTAGCCATGGCGTTAGTA-3' (C69F28) <SEQ ID NO. 1>, 5'-GGGAGAGCCATAGTGGTCTGCGGAA-3' (C131F25) <SEQ ID NO. 2>, or 5'-GTGGTCTGCGGAACCGGTGAGTACAC-3 (C143F26) <SEQ ID NO. 3>; and the reverse primers may be 5'-CGGTTCCGCAGACCACTATGGCTCTC-3' (C133R26) <SEQ ID NO. 4>, 5'-GCAAGCACCCTATCAGGCAGTACCACA-3' (C282R27) <SEQ ID NO. 5>, 5'-CACTCGCAAGCACCCTATCAGGCAGTA-3' (C287R27) <SEQ ID NO. 6>, or 5'-CGGGGCACTCGCAAGCACCCTATCA-3' (C294R25) <SEQ ID NO. 7>.

Kits for amplifying HCV DNA derived from HCV RNA can also be prepared containing one or more pairs of forward and reverse 3' NCR oligonucleotide primers, where the forward primer may be 5'-GGTGGCTCCATCTTAGCCCTAGTCACG-3' (1F27) <SEQ ID NO. 8> and the reverse primer may be the oligonucleotide 5'-AGGCCAGTATCAGCACTCTCTGCAGTC-3 (57R27) <SEQ ID NO. 9>.

Kits for detecting the presence of HCV DNA, which comprise the 5' and 3'NCR primers described above for amplification of HCV DNA derived from HCV RNA are also encompassed within the scope of the invention.

The kits may additionally comprise reagents and instructions for reverse transcription, amplification, and product detection. For example, the kits can contain reverse transcriptase, deoxynucleotides, thermostable polymerases suitable for DNA amplification reactions, and reagents for labeling and detection of nucleic acids.

The present invention finds use in the diagnosis of HCV infection in patients; in testing the efficacy of anti-HCV therapeutic regimens; and in screening the blood supply for HCV-infected samples.

DESCRIPTION OF THE PREFERRED EMBODIMENTS

The following examples illustrate the present invention without limitation.

Example 1

Detection of HCV in Biological Samples: Comparison of 5' HCV Amplification Primers and Roche Amplicor HCV Assay The following experiments were performed to compare the HCV assay of the present invention with the Roche Amplicor system.

A. Methods:

1. Sample preparation:

RNA was prepared from plasma samples using PureScript® RNA isolation reagents (Gentra Systems, Minneapolis Minn.). Modifications to the manufacturer's protocol for body fluids included use of 40 µg glycogen, rather than 20 µg, as a carrier to aid in the precipitation of viral RNA. Additionally, in most cases, after isopropyl alcohol precipitation of the RNA and washing the RNA pellet with ethanol, the RNA pellet was resuspended in the RT buffer mix, rather than in the RNA hydration solution provided by the manufacturer.

2. Reverse Transcription:

The synthesis of cDNA from RNA was catalyzed by the addition of 100 U recombinant Moloney Murine Leukemia Virus (M-MLV) reverse transcriptase (RT) (Gibco BRL, Gaithersburg, Md.) in a 50 µl solution of 50 mM Tris-HCl (pH 8.3), 75 mM KCl, 3 mM $MgCl_2$, 10 mM DTT, 0.4 mM of each dNTP (Pharmacia Biotech), 4 µM random hexamers (Pharmacia Biotech, Piscataway, N.J.) or specific reverse transcription primer, and 20 units RNasin (Promega, Madison, Wis.) in diethylpyrocarbonate (DEPC)-treated water. After incubation at 42° C. for 30 min, the RT reaction was held at 100° C. for 5 min to destroy RT activity. Each reaction was chilled for 1 min followed by microcentrifugation at 16000×g for 4 seconds.

3. PCR amplification:

PCR was carried out IN A PE9600 thermocycler (PerkinElmer) in a 100 µl solution of 25 mM Tris-HCl, 3 mM $MgCl_2$, 0.725 mM EDTA, 54 mM KCl, 3.72 mM NaCl, 40 µM DTT, 108 µg/mL gelatin (type IV), 9.5% glycerol, 0.02% Tween 20, 0.02% NP40, calf thymus DNA (2 µg), 1.2 mM of each dNTP, 0.4 µM of each primer, 10 copies linearized internal positive control (IPC) plasmid DNA, and 16 U of Taq polymerase. Monoclonal antibodies to Taq, TP1-12 and TP4-9, the preparation of which are disclosed in U.S. Pat. No. 5,338,671, were added to the reaction at a 50:1 and 5:1 molar ratio, respectively, to provide a 55:1 molar ratio of antibody to Taq polymerase. After initial denaturation at 96° C. for 3 min, 40 cycles of amplification were performed at 96° C. for 5 sec and 68° C. for 40 sec. At the conclusion of cycling, a post-heat step was performed for 5 min at 103° C. to inactivate Taq polymerase. The primers used are shown in Table 2 below.

TABLE 2

| PRIMER | SEQUENCE | LOC. | S* | SIN** |
|---|---|---|---|---|
| C69f28 | 5'-CAGAAAGCGTCTAGCCATGGCGTTAGTA-3' | 69–96 | S | 1 |
| C131F25 | 5'-GGGAGAGCCATAGTGGTCTGCGGAA-3' | 131–155 | S | 2 |
| C143F26 | 5'-GTGGTCTGCGGAACCGGTGAGTACAC-3' | 143–168 | S | 3 |

TABLE 2-continued

| PRIMER | SEQUENCE | LOC. | S* | SIN** |
|---|---|---|---|---|
| C133R26 | 5'-CGGTTCCGCAGACCACTATGGCTCTC-3' | 133–158 | AS | 4 |
| C282R26 | 5'-GCAAGCACCCTATCAGGCAGTACCACA-3' | 282–308 | AS | 5 |
| C287R27 | 5'-CACTCGCAAGCACCCTATCAGGCAGTA-3' | 287–313 | AS | 6 |
| C294R25 | 5'-CGGGGCACTCGCAAGCACCCTATCA-3' | 294–318 | AS | 7 |

*Strand orientation: S = sense; AS = antisense; **Sequence ID No.

The predicted product sizes are shown in Table 3 below.

TABLE 3

| FORWARD | REVERSE | PRODUCT SIZE (bp) |
|---|---|---|
| C69F28 | C133R26 | 90 |
| C131F25 | C294R25 | 188 |
| C143F26 | C282R27 | 166 |
| C143F26 | C282R27 | 171 |

4. Detection of PCR products:

PCR products were biotinylated by use of 5'-biotin-labeled primers (sense strand) during amplification. Product was captured by hybridization to oligonucleotide probes covalently attached to latex particles, which were deposited on the surface of a flow through membrane (SureCell® tests, Ortho Clinical Diagnostics, Rochester, N.Y.). The probes were: 5'-GGGTCCTGGAGGCTGCACGACACTCAT-3' (designated C96-27-PRB) <SEQ ID NO. 11>; 5'-CCTTTCGCGACCCAACACTACTCGGCT-3' (designated C252-27-PRB) <SEQ ID NO. 12>; and 5'-TTTCGCGACCCAACACTACTCGGCT-3' (designated C252-25-PRB) <SEQ ID NO. 13>. The probe/product complex was reacted with streptavidin (SA)-horseradish peroxidase (HRP) conjugate, which catalyzes the oxidative conversion of a dye precursor to a dye (blue color). The blue color intensity was scored visually (0–10) by comparing color intensity to color standards. All visual color scores >3 were considered to be positive results.

5. Roche Amplicor Assay:

The Roche Amplicor assay (Roche Diagnostics, Kaiseraugst, Switzerland) was performed according to the manufacturer's instructions.

B. Results:

A panel of 42 samples from Brazilian and Egyptian patients was tested for HCV as described above. Some of the samples were also tested using the Chiron B-DNA assay. Brazilian samples were expected to contain a larger proportion of HCV genotype 3 compared to US samples and the Egyptian samples were expected to consist of mostly HCV genotype 4, a genotype rarely found in the US.

All reactions were performed in duplicate. A positive score indicates that both duplicates were positive. The results are shown in Table 4 below.

TABLE 4

| Country | bDNA c/ml | Roche Amplicor | 131F/294 R 5'NC (Jun. 18, 1997) | 69F/133 R 5'NC | 143F/283 R 5'NC | 143F/287 R 5'NC |
|---|---|---|---|---|---|---|
| Brazil | 1258000 | + | + | + | ND | ND |
| Brazil | ND | − | − | − | ND | ND |
| Brazil | ND | − | − | − | ND | ND |
| Brazil | 2265000 | + | + | + | ND | ND |
| Brazil | ND | + | + | + | ND | ND |
| Brazil | ND | − | − | − | ND | ND |
| Brazil | 253000 | −/− | + | + | + | + |
| Brazil | 524000 | + | + | + | ND | ND |
| Brazil | ND | − | − | − | ND | ND |
| Brazil | ND | + | + | + | + | + |
| Brazil | 2089000 | + | + | + | ND | ND |
| Brazil | 391000 | + | + | + | ND | ND |
| Brazil | ND | −/+ | + | + | + | + |
| Brazil | 234000 | + | + | + | ND | ND |
| Brazil | ND | − | +/− | +/− | − | − |
| Brazil | 371000 | + | + | + | ND | ND |
| Brazil | 703000 | + | + | + | ND | ND |
| Brazil | ND | − | − | − | − | − |
| Brazil | 298000 | + | + | + | ND | ND |
| Brazil | 251000 | + | + | + | ND | ND |
| Brazil | 267000 | + | + | + | ND | ND |
| Brazil | 503000 | + | + | + | ND | ND |
| Egypt | ND | − | +/− | + | − | +/− |
| Egypt | ND | + | + | + | ND | ND |
| Egypt | ND | − | + | + | + | + |

TABLE 4-continued

| Country | bDNA c/ml | Roche Amplicor | 131F/294R 5'NC (Jun. 18, 1997) | 69F/133 R 5'NC | 143F/283 R 5'NC | 143F/287 R 5'NC |
|---|---|---|---|---|---|---|
| Egypt | ND | – | +/– | + | – | – |
| Egypt | ND | + | + | + | ND | ND |
| Egypt | ND | + | + | + | ND | ND |
| Egypt | ND | – | – | +/– | – | – |
| Egypt | ND | + | + | + | ND | ND |
| Egypt | ND | + | + | + | +/– | – |
| Egypt | ND | – | – | – | ND | ND |
| Egypt | ND | – | – | + | – | – |
| Egypt | 566000 | – | + | + | ND | ND |
| Egypt | 205000 | – | + | + | +/– | + |
| Egypt | ND | – | – | – | ND | ND |
| Egypt | ND | + | + | + | ND | ND |
| Egypt | ND | – | +WK | + | – | – |
| Egypt | ND | – | – | + | – | – |
| Egypt | ND | – | – | + | – | – |
| Egypt | ND | – | – | +/– | ND | ND |
| Egypt | ND | + | + | + | + | + |

A comparison between the results obtained using the 5' NCR primers of the present invention and the Roche assay system is summarized in Tables 5 and 6 below:

TABLE 5

Roche Amplicor

| C131/C294 (long product) | + | – |
|---|---|---|
| + | 21 | 5 |
| – | 0 | 16 |

TABLE 6

Roche Amplicor

| 69F/133R (short product) | + | – |
|---|---|---|
| + | 21 | 11 |
| – | 0 | 10 |

All of the primers of the invention demonstrated superior sensitivity when compared to the Roche Amplicor assay. Use of the primer pair 69F/133R afforded the greatest sensitivity. Five samples that were negative using the Roche amplicor assay were positive using the C131/C294 primer pair of the present invention, while 11 samples that were negative using the Roche amplicor assay were positive using the 69F/133R primer pair of the present invention. Furthermore, all of the samples with viral loads detectable by the Chiron bDNA assay were detected using the primers of the present invention, whereas three of these were not detected using the Roche Amplicor assay. None of the negative controls were scored as positive in the assay according to the present invention.

In a second series of experiments, 150 plasma samples from Brazil that were previously determined to be positive for HCV antibody were tested in the Roche Amplicor assay and using the primers of the present invention. Tables 7 and 8 below show results based on SureCell® color scores. For each reaction, the products were examined on gels to confirm the results. Negative controls (interspersed throughout the clinical samples) consisting of both negative plasma samples and water (no RNA) were included for each primer set. All negative control results were negative.

TABLE 7

Roche Amplicor

| 131F/294R | + | – |
|---|---|---|
| + | 90 | 4 |
| – | 0 | 56 |

TABLE 8

Roche Amplicor

| 69F/133R | + | – |
|---|---|---|
| + | 90 | 7 |
| – | 0 | 53 |

Both 5' NCR primer pairs according to the present invention exhibited superior sensitivity relative to the Roche assay system. The greatest sensitivity was achieved using the 69F/133R primer pair, which detected the presence of HCV RNA in three additional samples compared to the C131/C294 primer pair.

Example 2

Analysis of Sensitivity of 5' NCR HCV Assays

The following experiments were performed to test the sensitivity of the HCV assay using the 5' NCR primer pairs of the present invention.

1. Three patient samples were diluted based on theoretical copy numbers of HCV RNA and assayed for HCV RNA using the Roche Amplicor system and the primer pairs of the present invention. The results are shown in Table 9 below.

TABLE 9

| JJCD code | Theoretical copies/ml | Roche Amplicor | 5' NC 131F/294R |
|---|---|---|---|
| A1 | 500 | + | + |
| A2 | 100 | + | + |
| A3 | 10 | − | + |
| A4 | 5 | − | + |
| A5 | 1 | − | − |
| B1 | 500 | + | + |
| B2 | 100 | + | + |
| B3 | 10 | + | + |
| B4 | 5 | + | + |
| B5 | 1 | + | + |
| C1 | 500 | + | + |
| C2 | 100 | + | + |
| C3 | 10 | − | + |
| C4 | 5 | − | ±/− |
| C5 | 1 | − | − |

In all three sets of diluted patient samples, the assay employing the 5' NCR primers of the present invention displayed greater sensitivity than the Roche assay.

2. Plasma known to be positive for HCV was diluted with HCV-negative plasma and tested as described above. An internal positive control (IPC) plasmid was incorporated into the reaction mixture at 10 copies/reaction. The results (a compilation of five experiments) are shown in Table 10 below.

TABLE 10

| Copies/ml | n | Copies/rxn. | 5' NC % pos. results | IPC % pos. results |
|---|---|---|---|---|
| 1000 | 24 | 50 | 100% | 100% |
| 200 | 24 | 10 | 100% | 100% |
| 100 | 59 | 5 | 100% | 100% |
| 20 | 64 | 1 | 69% | 100% |

The C131F/C294R 5' NCR primer pair exhibited excellent sensitivity and was able to detect as little as a single viral particle per PCR reaction as predicted by a Poisson distribution analysis.

3. Eighteen patient samples from patients with low HCV viral loads (range=316–8080 copies/ml, which corresponds to 16–404 copies/PCR reaction).

Seventeen of the eighteen samples tested positive in the present assay.

Example 3

Detection of HCV in Biological Samples:
Comparison of 3' NCR HCV Amplification Primers and Roche Amplicor HCV Assay 150 plasma samples from Brazil that were previously determined to be positive for HCV antibody were tested in the Roche Amplicor assay and using the 3' NCR primers of the present invention. Reverse transcription and amplification were performed as described in Example 1 above. Reverse transcription was performed using the a primer with the sequence 5'-GTATCAGCACTC-3' <SEQ ID NO. 16>, and amplification was performed using the X1F27/57R27 primer pair. Each reaction contained an internal positive control (IPC) of plasmid DNA. Detection of amplification products was performed using the SureCell® system, using as a capture probe 3×30PRB25. For each reaction, the products were examined on gels to confirm the results. Negative controls (interspersed through out the clinical samples) consisting of both negative plasma samples and water (no RNA) were included and all were negative in RT-PCR. A comparison between the results obtained using the primers of the present invention and the Roche assay system is summarized in Table 11.

TABLE 11

| ROCHE AMPLICOR | | |
|---|---|---|
| | + | − |
| 1F27/57R2 + | 85 | 0 |
| 3' Assay − | 3 | 62 |

Example 4

Detection of HCV in Biological Samples:
Comparison of the Present Invention and Rochester General Hospital (RGH) 5' NCR Nested PCR Assay The following experiment was performed to compare the 3' NCR HCV primers of the present invention with the RGH Nested PCR detection system.

Eighty three plasma samples were reverse-transcribed using the 57R27 primer and the reverse transcription products were amplified using the 3X1F27/57R27 primer pair using the methods described in Example 1 above. For each reaction, the products were examined on gels to confirm the results. Negative controls (interspersed through out the clinical samples) consisting of both negative plasma samples and water (no RNA) were included and all were negative in this assay.

A comparison between the results obtained using the primers of the present invention and the Roche assay system is summarized in Table 12.

TABLE 12

| 5' NESTED ASSAY (RG) | | |
|---|---|---|
| | + | − |
| 1F27/57R2 + | 56 | 1 |
| 3' Assay − | 1 | 25 |

These results demonstrate that the detection system of the present invention is both sensitive and specific when compared with the RGH nested PCR system. The assay according to the invention agreed with the RGH assay on 25 of the 26 negative samples. The advantage of the present invention is that there is less chance of carryover than when performing nested PCR, as in the latter, the tube must be opened during the reaction to add new reagents. The single sample which indicates a false negative result could be an example of carryover caused by the nested PCR protocol.

Example 5

Copy Sensitivity of the 3' NCR HCV Assay

The following experiment was performed to determine the detection sensitivity of the 3' NCR HCV assay of the present invention.

Plasma samples, which had been tested for HCV using the Roche Monitor and Chiron B-DNA assays, were obtained from Boston Biomedica, Inc. RNA was prepared, diluted to contain between 20–1000 copies of HCV RNA/ml, and subjected to reverse transcription and amplification using the methods described in Example 1 above. Reverse transcription was performed using the 66RT (12-mer) primer (Table 13) or 57R27 (27-mer) primer (Table 14), and PCR was performed using 1F27 and 57R27 forward and reverse primers, respectively. Internal positive control (IPC) primers were also incorporated into this assay and resulted in positive scores for each sample. Results represent the % of samples that were positive based on gel bands and Sure-Cell® using 3X-30PRB25 as a capture probe.

TABLE 13

| n | Copies/ml | Copies/rxn. | % pos. results |
|---|---|---|---|
| 16 | 1000 | 50 | 100% |
| 16 | 200 | 10 | 88% |
| 57 | 100 | 5 | 49% |
| 64 | 20 | 1 | 20% |

TABLE 14

| n | Copies/rxn | Average Visible Color | % pos. results |
|---|---|---|---|
| 9 | 50 | 8 | 100% |
| 10 | 10 | 8 | 100% |
| 10 | 0 | 0 | 0% |

The 3' NCR HCV assay detected 1000 viral copies/ml 100% of the time, and 200 copies/ml 88–100% of the time. At 100 copies/ml, virus was detected in approximately 50% of the samples (when using a 12-mer RT primer). A Poisson distribution would predict that at 1 copy per reaction (20 viral particles/ml), the frequency of positive results should be approximately 60%. The finding of 20% detection at this level of virus may be due to the possibility that the 3' non-coding region of HCV is not present in every viral particle, or that there is an inherent sensitivity loss in this assay when using short (12-mer) reverse transcription primers. The latter explanation was supported by performing a reverse transcription/amplification assay on the same samples using 5' NCR primers, which resulted in a higher level of detection at 20 copies/ml. These results indicate that the sensitivity of the 3'NC assay could be increased by using longer (27-mer) primers for reverse transcription (compare the detection of 10 copies/rxn using 12-mer and 27-mer primers, Tables 13 and 14, respectively).

Example 6

Analysis of Patient Samples Having Different HCV Genotypes

The following experiments were performed to assess the detection of HCV having different genotypes.
1. Genotype inclusivity:
Chimpanzee plasma, representing various genotypes of HCV, was obtained from National Institutes of Health (NIH). Plasma was prepared and treated as described in Example 1 above. The 5' NCR primers were C131F and C294R (forward and reverse primers, respectively) and the 3' NCR primers were 1F27 and 57R27 (forward and reverse primers, respectively). The results were obtained by analysis of PCR products on 4% agarose gels stained with ethidium bromide. Positive results were based on replicate samples. The results are show in Table 15 (using 5' NCR primers) and Table 16 (using 3' NCR primers) below.

TABLE 15

| Genotype | Strain | % pos. results |
|---|---|---|
| 1a | H77 | + |
| 1b | H-J4 | + |
| 2a | H-J6 | + |
| 2b | C-J8 | + |
| 3a | S52 | + |
| 5a | SA13 | + |

TABLE 16

| n | genotype | strain | #copies/rxn | % pos. results |
|---|---|---|---|---|
| 4 | 1a | H77 | 100 | 100% |
| 4 | 1b | H-J4 | 100 | 100% |
| 4 | 2a | H-J6 | 100 | 100% |
| 4 | 2b | C-J8 | 100 | 100% |
| 4 | 3a | S52 | 100 | 100% |
| 4 | 5a | SA13 | 100 | 100% |

2. Patient samples:
Twenty seven undiluted patient samples of known genotype were assayed using the C131F and C294R primers as described above. SureCell® detection was used to confirm results (using C252-PRB25 and IPC-1P as the capture probe HCV and IPC products, respectively). The panel included representative plasma samples infected with HCV genotypes 1 through 4 and 6. Patient samples were from various geographic regions (Scotland, Tunisia, Saudi Arabia, and Hong Kong). Each sample was tested in duplicate (for example, 6 genotype 1 samples were tested).

The primer system of the present invention was able to amplify all the genotype samples included in this panel. The C131F25/C294R25 primers identified all possible HCV genotypes to date (Genotypes 1–6).
3. Low copy number samples:
Samples containing HCV of different genotypes (1–6, obtained from the US, Scotland, Tunisia, Saudi Arabia, and Hong Kong) were quantified using the Roche Monitor Assay, diluted to 50 viral copies per PCR reaction (1000 copies/mL), and assayed using the C131F and C294R primers as described above.

All samples were detected using the primers of the present invention.

Example 7

Multiplex Assays Using Both 5' and 3' Amplification Primer Pairs

The following experiments were performed to analyze the effect of simultaneous amplification of 5' NCR and 3' NCR regions of the HCV genome in a single reaction mixture.
A. Comparison with Roche Monitor Assay:
73 patient samples, containing the equivalent of between 45 and 170,000 viral copies per reaction, were tested. The samples were from patients known to be infected with HCV who had been treated with interferon. As a consequence, some patients had little or no circulating virus. This panel was tested in a multiplex format using the 5' NCR primer pair 131F/294R and the 3' NCR primer pair 1F27/57R27, as well as IPC primers. Negative clinical samples were placed through out the test samples. All negatives resulted in a negative RT-PCR. The results were compared with those obtained using the quantitative Roche Monitor Assay (Roche Diagnostics, Kaiseraugst, Switzerland). The results are summarized in Table 17 below.

TABLE 17

ROCHE MONITOR

|  |  | + | − |
|---|---|---|---|
| Multiplexed | + | 60 | 1 |
| Assay | − | 0 | 12 |

When using the 5' and 3' NCR primer pairs of the invention, an additional sample that was undetectable according to the Roche Monitor Results was detected with the 5' NCR and 3' NCR assays which indicates that the assays utilizing the primers of the present invention show greater sensitivity than the Roche assay when assaying samples with low viral loads. This positive sample, which went undetected by the Roche assay, was confirmed using alternate 5' NCR primers 69F/133R.

B. Comparison with Roche Amplicor Assay:

Sixteen patient samples that had tested as indeterminate using a recombinant immunoblot assay (RIBA) were tested in a multiplex format using the 5' primer pair 131F/294R and the 3' primer pair 1F27/57R27. The results were compared with those obtained using the qualitative Roche Amplicor assay. The results are summarized in Table 18 below.

TABLE 18

ROCHE AMPLICOR

|  |  | + | − |
|---|---|---|---|
| Multiplexed | + | 4 | 0 |
| Assay | − | 0 | 12 |

There was 100% concordance between the assay of the invention and the Roche assay. All PCR reactions were done in duplicate from a single RNA extraction. The negatives were confirmed by amplification using an alternative 5' NC primer set (69F/133R). All negatives re-tested were confirmed as "true" negatives.

All patents, applications, articles, publications, and test methods mentioned above are hereby incorporated by reference in their entirety. Many variations of the present invention will suggest themselves to those skilled in the art in light of the above detailed description. Such obvious variations are within the full intended scope of the appended claims.

What is claimed is:

1. A method for detecting the presence of Hepatitis C Virus (HCV) RNA in a biological sample, said method comprising:

(A) performing a reverse transcription reaction using, as a template, RNA derived from said sample to produce HCV-specific reverse transcription products;

(B) amplifying said reverse-transcription products using one or more pairs of oligonuclecotide primers specific for HCV to produce HCV-specific amplification products, wherein said pairs are selected fom the group consisting of:

(a) forward primer 5'-CAGAAAGCGTCTAGCCATGGCGTTAGTA-3' (C69F28) <SEQ ID NO. 1> and reverse primer 5'-CGGTTCCGCAGAGACCACTATGGCTCTC-3' (C133R26) <SEQ ID NO. 4>; and (b) forward primer 5'-GGGAGAGCCATAGTGGTCTGCGGAA-3' (C131F25) <SEQ ID NO. 2> and reverse primer 5'-CGGGGCACTCGCAAGCACCCTATCA-3' (C294R26) <SEQ ID NO. 7>; and (C) detecting said amplifcation products, wherein detection of said amplification products indicates the presence of HCV RNA in said sample.

2. A method as defined in claim 1, wherein said reverse transcriptase reaction is performed using random oligonucleotide primers.

3. A method as defined in claim 1, wherein said reverse transcription reaction is performed using one or more oligonucleotide primers having sequences corresponding to sequences in HCV RNA.

4. A method as defined in claim 1, wherein said amplifying is performed by a method selected from the group consisting of polymerase chain reaction, ligase chain reaction, strand displacement amplification, nucleic acid single base substitution, and transcription mediated amplification.

5. A method as defined in claim 1, wherein said detecting comprises visualizing said amplification products by gel electrophoresis.

6. A method as defined in claim 1, wherein said detecting comprises capturing said amplification products on a solid support containing one or more HCV-specific oligonucleotide probes and quantifying said captured products using a colorimetric assay.

7. A method as defined in claim 6, wherein said probes comprise a member selected from the group consisting of:
(a) 5'-TTTCGCGACCCAACACTACTCGGCT-3' (C252-25-PRB) <SEQ ID NO. 13> and
(b) 5'-CCTTTCGCGACCCAACACTACTCGGCT-3' (C252-27-PRB) <SEQ ID NO. 12> when said forward primer is (C131F25); and
wherein said probes comprise
(c) 5'-GGGTCCTGGAGGCTGCACGACACTCAT-3' (C96-22-PRB) <SEQ ID NO. 11> when said forward primer is (C69F28).

8. A method as defined in claim 1, wherein said sample is selected from the group consisting of blood, serum, plasma, urine, saliva, and cerebrospinal fluid.

9. A method for amplifying Hepatitis C Virus (HCV) DNA, which method comprises performing a polymerase chain reaction on a DNA sample containing HCV DNA using one or more pairs of oligonucleotide primers specific for HCV to produce HCV-specific amplification products, wherein said parrs are selected from the group consisting of:
(a) forward primer 5'-CAGAAAGCGTCTAGCCATGGCGTTAGTA-3' (C69F28) <SEQ ID NO. 1> and reverse primer 5'-CGGTTCCGCAGACCACTATGGCTCTC-3' (C133R28) SEQ ID NO. 4>; and
(b) forward primer 5'-GGGAGAGCCATAGTGGTCTGCGGAA-3' (C131F25) <SEQ ID NO. 2> and reverse primer 5'-CGGGGCACTCGCAAGCACCCTATCA-3' (C294R25) <SEQ ID NO. 7>.

10. A method as defined in claim 9, which method further comprises detecting said amplification products, wherein detection of said amplification products indicates the presence of HCV DNA in said sample.

11. A method as defined in claim 10, wherein said detecting comprises visualizing said amplification products by gel electrophoresis.

12. A method as defined in claim 10, wherein said detecting comprises capturing said amplification products on a solid supporr containing one or more HCV-specific oligonucleotide probes and quantifying said captured products using a colorimetric assay.

13. A method as defined in claim 12, wherein said probes comprise a member selected from the group consisting of:
(a) 5'-TTTCGCGACCCAACACTACTCGGCT-3' (C252-25-PRB) <SEQ ID NO. 13> and
(b) 5'-CCTTTCGCGACCCAACACTACTCGGCT-3' (C252-27-PRB) <SEQ ID NO. 12> when said forward primer is (C131F25); and
wherein said probes comprise
(c) 5'-GGGTCCTGGAGGCTGCACGACACTCAT-3' (C96-22-PRB) <SEQ ID NO. 11> when said forward primer is (C69F28).

14. A method for detecting the presence of Hepatitis C Virus (HCV) RNA in a biological sample, said method comprising:
(A) performing a reverse transcription reaction using as a template RNA derived from said sample to produce HCV-specific reverse transcription products;
(B) amplifying said reverse-transcription products using one or more pairs of 5' NCR oligonucleotide primers specific for HCV and one or more pairs of 3' NCR oligonucleotide primers to produce HCV-specific amplification products,
wherein said 5' NCR primer pairs are selected from the group consisting of:
(a) forward primer 5'-CAGAAAGCGTCTAGCCATGGCGTTAGTA-3' (C69F28) <SEQ ID NO. 1> and reverse primer 5'-CGGTTCCGCAGACCACTATGGCTCTC-3' (C133R26) <SEQ ID NO. 4>; and
(b) forward primer 5'-GGGAGAGCCATAGTGGTCTGCGGAA-3' (C131 F25) <SEQ ID NO. 2> and reverse primer 5'-CGGGGCACTCGCAAGCACCCTATCA-3' (C294R25) <SEQ ID NO. 7>; and
wherein each of said pairs of 3' NCR oligonucleotide primers comprises a forward primer consisting of the oligonucleotide 5'-GGTGGCTCCATCTTAGCCCTAGTCACG-3' (1F27) <SEQ ID NO. 8> and a reverse primer consisting of the oligonucleotide 5'-AGGCCAGTATCAGCACTCTCTGCAGTC-3' (57R27) <SEQ ID NO. 9>; and
(C) detecting said amplification products, wherein detection of said amplification products indicates the presence of HCV RNA in said sample.

15. A method as defined in claim 14, wherein said reverse transcription reaciton is performed using random oligonucleotide primers.

16. A method as defined in claim 14, wherein said reverse transcription reaction is performed using one or more oligonucleotide primers having sequences corresponding to sequences in HCV RNA.

17. A method as defined in claim 14, wherein said amplifying is performed by a method selected from the group consisting of polymerase chain reaction, ligase chain reaction, strand displacement amplification, nucleic acid single base substitution, and transcription mediated amplification.

18. A method as defined in claim 14, wherein said detecting comprises visualizing said amplification products by gel electrophoresis.

19. A method as defined in claim 14, wherein said detecting comprises capturing said amplification products on a solid support containing one or more HCV-specific oligonucleotide probes and quantifying said captured products using a colorimetric assay.

20. A method as defined in claim 19, wherein said probes comprises a member selected from the group consisting of:
(a) 5'-TTTCGCGACCCAACACTACTCGGCT-3' (C252-25-PRB) <SEQ ID NO. 13> and
(b) 5'-CCTTTCGCGACCCAACACTACTCGGCT-3' (C252-27-PRB) <SEQ ID NO. 12> when said 5' NCR forward primer is (C131F25);
wherein said probes comprise
(c) 5'-GGGTCCTGGAGGCTGCACGACACTCAT-3' (C98-22-PRB) <SEQ ID NO. 11> when said 5' NCR forward primer is (C69F28); and
wherein said probes comprise a member selected from the group consisting of
(d) 5'-GCGGCTCACGGACCTTTCACAGCTA-3' (30PRB26) <SEQ ID NO. 14>; and
(e) 5'-ATGCGGCTCACGGACCTTTCACAGC-3' (32PRB25) <SEQ ID NO. 15>.

21. A method as defined in claim 14, wherein said sample is selected from the group consisting of blood, serum, plasma, urine, saliva, and cerebrospinal fluid.

22. A method for amplifying Hepatitis C Virus (HCV) DNA, which method comprises performing a polymerase chain reaction on a DNA sample containing HCV DNA using one or more pairs of 5' NCR oligonucleotide primers specific for HCV and one or more pairs of 3' NCR oligonucleotide primers to produce HCV-specific amplification products, wherein said 5' NCR primer pairs are selected from the group consisting of:
(a) forward primer 5'-CAGAAAGCGTCTAGCCATGGCGTTAGTA-3' (C69F28) <SEQ ID NO. 1> and reverse primer 5'-CGGTTCCGCAGACCACTATGGCTCTC-3' (C133R26) <SEQ ID NO. 4>; and
(b) forward primer 5'-GGGAGAGCCATAGTGGTCTGCGGAA-3' (C131F25) <SEQ ID NO. 2> and reverse primer 5'-CGGGGCACTCGCAAGCACCCTATCA-3' (C294R25) <SEQ ID NO. 7>; and
wherein each of said pairs of 3' NCR oligonucleotide primers comprises a forward primer consisting of the oligonucleotide 5'-GGTGGCTCCATCTTAGCCCTAGTCACG-3' (1F27) <SEQ ID NO. 8> and a reverse primer consisting of the oligonucleotide 5'-AGGCCAGTATCAGCACTCTCTGCAGTC-3' (57R27) <SEQ ID NO. 9>.

23. A method as defined in claim 22, which method further comprises detecting said amplification products, wherein detection of said amplification products indicates the presence of HCV DNA in said sample.

24. A method as defined in claim 23, wherein said detecting comprises visualizing said amplification products by gel electrophoresis.

25. A method as defined in claim 23, wherein said detecting comprises capturing said amplification products on a solid support containing one or more HCV-specific oligonucleotide probes and quantifying said captured products using a colorimetric assay.

26. A method as defined in claim 25, wherein said probes comprise a member selected from the group consisting of:
(a) 5'-TTTCGCGACCCAACACTACTCGGGCT-3' (C252-25-PRB) <SEQ ID NO. 13> and
(b) 5'-CCTTTCGCGACCCAACACTACTCGGCT-3' (C252-27PRB) <SEQ ID NO. 12> when said 5' NCR forward primer is (C131F25);
wherein said probes comprise
(c) 5'-GGGTCCTGGAGGCTGCACGACACTCAT-3' (C96-22-PRB) <SEQ ID NO. 11> when said 5' NCR forward primer is (C69F28); and
wherein said probes comprise a member selected from the group consisting of
(d) 5'-GCGGCTCACGGACCTTTCACAGCTA-3' (30PRB25) <SEQ ID NO. 14>; and
(e) 5'-ATGCGGCTCACGGACCTTTCACAGC-3' (32PRB25) <SEQ ID NO. 15>.

27. A kit for amplifying HCV DNA derived from HCV RNA, said kit comprising one or more pairs of 5' NCR oligonucleotide primers, wherein said 5' NCR primer pairs are selected from the group consisting of:
(a) forward primer 5'-CAGAAAGCGTCTAGCCATGGCGTTAGTA-3' (C69F28) <SEQ ID NO. 1> and reverse primer 5'-CGGTTCCGCAGACCACTATGGCTCTC-3' (C133R26) <SEQ ID NO. 4>; and
(b) forward primer 5'-GGGAGAGCCATAGTGGTCTGCGGAA-3' (C131F25) <SEQ ID NO. 2> and reverse primer 5'-CGGGGCACTCGCAAGCACCCTATCA-3' (C294R25) <SEQ ID NO. 7>.

28. A kit as defined in claim 27, further comprising one or more pairs of 3' NCR oligonucleotide primers, wherein each of said pairs of 3' NCR oligonucleotide primers comprises a forward primer consisting of the oligonucleotide 5'-GGTGGCTCCATCTTAGCCCTAGTCACG-3' (1F27) <SEQ ID NO. 8> and a reverse primer consisting of the oligonucleotide 5'-AGGCCAGTATCAGCACTCTCTGCAGTC-3 (57R27) <SEQ ID NO. 9>.

29. A kit as defined in claim 27, further comprising one or more probes.

30. A kit as defined in claim 28, further comprising one or more probes.

31. A kit as defined in claim 29, wherein said probes comprise a member selected from the group consisting of:
(a) 5'-TTTCGCGACCCAACACTACTCGGCT-3' (C252-25-PRB) <SEQ ID NO. 13> and
(b) 5'-CCTTTCGCGACCCAACACTACTCGGCT-3' (C252-27-PRB) <SEQ ID NO. 12> when said 5' NCR forward primer is (C131F25); and
wherein said probes comprise
(c) 5'-GGGTCCTGGAGGCTGCACGACACTCAT-3' (C96-22-PRB) <SEQ ID NO. 11> when said 5' NCR forward primer is (C69F28).

32. A kit as defined in claim 30, wherein said probes comprise a member selected from the group consisting of:
(a) 5'-TTTCGCGACCCAACACTACTCGGCT-3' (C252-25-PRB) <SEQ ID NO. 13> and
(b) 5'-CCTTCGCGACCCAACACTACTCGGCT-3' (C252-27-PRB) <SEQ ID NO. 12> when said 5' NCR forward primer is (C131F25);
wherein said probes comprise
(c) 5'-GGGTCCTGGAGGCTGCACGACACTCAT-3' (C98-22-PRB) <SEQ ID NO. 11> when said 5' NCR forward primer is (C69F28); and
wherein said probes comprise a member selected from the group consisting of
(d) 5'-GCGGCTCACGGACCTTTCACAGCTA-3' (30PRB25) <SEQ ID NO. 14>; and
(e) 5'-ATGCGGCTCACGGACCTTTCACAGC-3' (32PRB25) <SEQ ID NO. 15>.

33. A kit as defined in claim 27, wherein said pair of 5' NCR primers consists of 5'-CAGAAAGCGTCTAGCCATGGCGTTAGTA-3' (C69F28) <SEQ ID NO. 1> and 5'-CGGTTCCGCAGACCACTATGGCTCTC-3' (C133R26) <SEQ ID NO. 4>.

34. A kit as defined in claim 27, wherein said pair of 5' NCR primers consists of 5'-GGGAGAGCCATAGTGGTCTGCGGAA-3' (C131F25) <SEQ ID NO. 2> and 5'-CGGGGCACTCGCAAGCACCCTATCA-3' (C294R25) <SEQ ID NO. 7>.

35. A kit for detecting the presence of HCV DNA, said kit comprising one or more pairs of 5' NCR oligonucleotide primers, wherein said 5' NCR primer pairs are selected from the group consisting of:
   (a) forward primer 5'-CAGAAAGCGTCTAGCCATGGCGTTAGTA-3' (C69F28) <SEQ ID NO. 1> and reverse primer 5'-CGGTTCCGCAGACCACTATGGCTCTC-3' (C133R26) <SEQ ID NO. 4>; and
   (b) forward primer 5'-GGGAGAGCCATAGTGGTCTGCGGAA-3' (C131F25) <SEQ ID NO. 2> and reverse primer 5'-CGGGGCACTCGCAAGCACCCTATCA-3' (C294R25) <SEQ ID NO. 7>.

36. A kit as defined in claim 35, further comprising one or more pairs of 3' NCR oligonucleotide primers, wherein each of said pairs of 3' NCR oligonucleotide primers comprises a forward primer consisting of the oligonucleotide 5'-GGTGGCTCCATCTTAGCCCTAGTCACG-3' (1F27) <SEQ ID NO. 8> and a reverse primer consisting of the oligonucleotide 5'-AGGCCAGTATCAGCACTCTCTGCAGTC-3 (57R27) <SEQ ID NO. 9>.

37. A kit as defined in claim 35, further comprising one or more probes.

38. A kit as defined in claim 36, further comprising one or more probes.

39. A kit as defined in claim 37, wherein said probes comprise a member selected from the group consisting of:
   (a) 5'-TTTCGCGACCCAACACTACTCGGCT-3' (C252-25-PRB) <SEQ ID NO. 13> and
   (b) 5'-CCTTTCGCGACCCAACACTACTCGGCT-3' (C252-27-PRB) <SEQ ID NO. 12> when said 5' NCR forward primer is (C131F25);

wherein said probes comprise
   (c) 5'-GGGTCCTGGAGGCTGCACGACACTCAT-3' (C96-22-PRB) <SEQ ID NO. 11> when said 5' NCR forward primer is (C69F28).

40. A method as defined in claim 38, wherein said probes comprise a member selected from the group consisting of:
   (a) 5'-TTTCGCGACCCAACACTACTCGGCT-3' (C252-25-PRB) <SEQ ID NO. 13> and
   (b) 5'-CCTTTCGCGACCCAACACTACTCGGCT-3' (C252-27-PRB) <SEQ ID NO. 12> when said 5' NCR forward primer is (C131F25);

wherein said probes comprise
   (c) 5'-GGGTCCTGGAGGCTGCACGACACTCAT-3' (C96-22-PRB) <SEQ ID NO. 11> when said 5' NCR forward primer is (C69F28); and wherein said probes comprise a member selected from the group consisting of
   (d) 5'-GCGGCTCACGGACCTTTCACAGCTA-3' (30PRB25) <SEQ ID NO. 14>; and
   (e) 5'-ATGCGGCTCACGGACCTTTCACAGC-3' (32PRB25) <SEQ ID NO. 15>.

41. A kit as defined in claim 35, wherein said pair of 5' NCR primers consists of 5'-CAGAAAGCGTCTAGCCATGGCGTTAGTA-3' (C69F28) <SEQ ID NO. 1> and 5'-CGGTTCCGCAGACCACTATGGCTCTC-3' (C133R26) <SEQ ID NO. 4>.

42. A kit as defined in claim 35, wherein said pair of 5' NCR primers consists of 5'-GGGAGAGCCATAGTGGTCTGCGGAA-3' (C131F25) <SEQ ID NO. 2> and 5'-CGGGGCACTCGCAAGCACCCTATCA-3' (C294R25) <SEQ ID NO. 7>.

* * * * *

SEQUENCE LISTING

```
<160> NUMBER OF SEQ ID NOS:  15

<210> SEQ ID NO 1
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 1
cagaaagcgt ctagccatgg cgttagta                                            28

<210> SEQ ID NO 2
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 2
gggagagcca tagtggtctg cggaa                                               25

<210> SEQ ID NO 3
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 3
gtggtctgcg gaaccggtga gtacac                                              26

<210> SEQ ID NO 4
<211> LENGTH: 26
<212> TYPE: DNA
<213> ORGANISM: Artificial Sequence
<220> FEATURE:
```

-continued

```
<223> OTHER INFORMATION: Oligonucleotide primer

<400> SEQUENCE: 4
cggttccgca gaccactatg gctctc                                           26

<210> SEQ ID NO 5
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 5
gcaagcaccc tatcaggcag taccaca                                          27

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 6
cactcgcaag caccctatca ggcagta                                          27

<210> SEQ ID NO 7
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 7
cggggcactc gcaagcaccc tatca                                            25

<210> SEQ ID NO 8
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 8
ggtggctcca tcttagccct agtcacg                                          27

<210> SEQ ID NO 9
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 9
aggccagtat cagcactctc tgcagtc                                          27

<210> SEQ ID NO 10
<211> LENGTH: 150
<212> TYPE: DNA
<213> ORGANISM: Artificial Sequence
<220> FEATURE:
<223> OTHER INFORMATION: target nucleic acid for an internal positive
      control

<400> SEQUENCE: 10
cgccagcgtg gaccatcaag tagtaatgaa cgcacggacg aggacatcat agagattaca      60
```

```
cctttatcca cagttctcgg tctaacgcag cagtcagtgt atcagcacca gcatccgtag    120
tgagtcttca gtgtctgctc caggatcgtg                                    150
```

```
<210> SEQ ID NO 11
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 11
gggtcctgga ggctgcacga cactcat                                        27

<210> SEQ ID NO 12
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 12
cctttcgcga cccaacacta ctcggct                                        27

<210> SEQ ID NO 13
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 13
tttcgcgacc caacactact cggct                                          25

<210> SEQ ID NO 14
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 14
gcggctcacg gacctttcac agcta                                          25

<210> SEQ ID NO 15
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 15
atgcggctca cggacctttc acagc                                          25
```